United States Patent [19]

Vermeiren

[11] Patent Number: 4,888,976

[45] Date of Patent: Dec. 26, 1989

[54] DEVICE FOR MEASURING THE EFFECTIVE VISCOSITY OF A LUBRICANT

[75] Inventor: Karel N. Vermeiren, Woerden, Netherlands

[73] Assignee: SKF Industrial Trading and Development Co. B.V., Nieuwegein, Netherlands

[21] Appl. No.: 921,624

[22] Filed: Oct. 21, 1986

[30] Foreign Application Priority Data

Oct. 22, 1985 [NL] Netherlands ............................ 8502876

[51] Int. Cl.$^4$ ..................... G01N 19/00; G01N 33/30
[52] U.S. Cl. ........................................................ 73/10
[58] Field of Search .................................. 73/10, 9, 64

[56] References Cited

U.S. PATENT DOCUMENTS

| | | | |
|---|---|---|---|
| 2,033,588 | 3/1936 | Pigott et al. | 73/10 |
| 4,253,326 | 3/1981 | Munnich et al. | 73/10 |
| 4,267,722 | 5/1981 | Hendry | 73/10 |
| 4,458,544 | 7/1984 | Gyer et al. | 73/864.87 |

*Primary Examiner*—Stewart J. Levy
*Assistant Examiner*—Robert R. Raevis
*Attorney, Agent, or Firm*—Rosen, Dainow & Jacobs

[57] ABSTRACT

A device for measuring the effective viscosity of a lubricant in which a motor rotates one element of a bearing with respect to the other, the lubricant being supplied to the bearing. The bearing is part of a sensor that outputs a signal corresponding to the percentage of contact time between the elements of the bearing. A speed regulator for the motor is responsive to the output of the sensor to maintain the speed of relative movement so that no roughness contacts occur in the bearing, at which time the motor speed is a measure of viscosity.

4 Claims, 1 Drawing Sheet

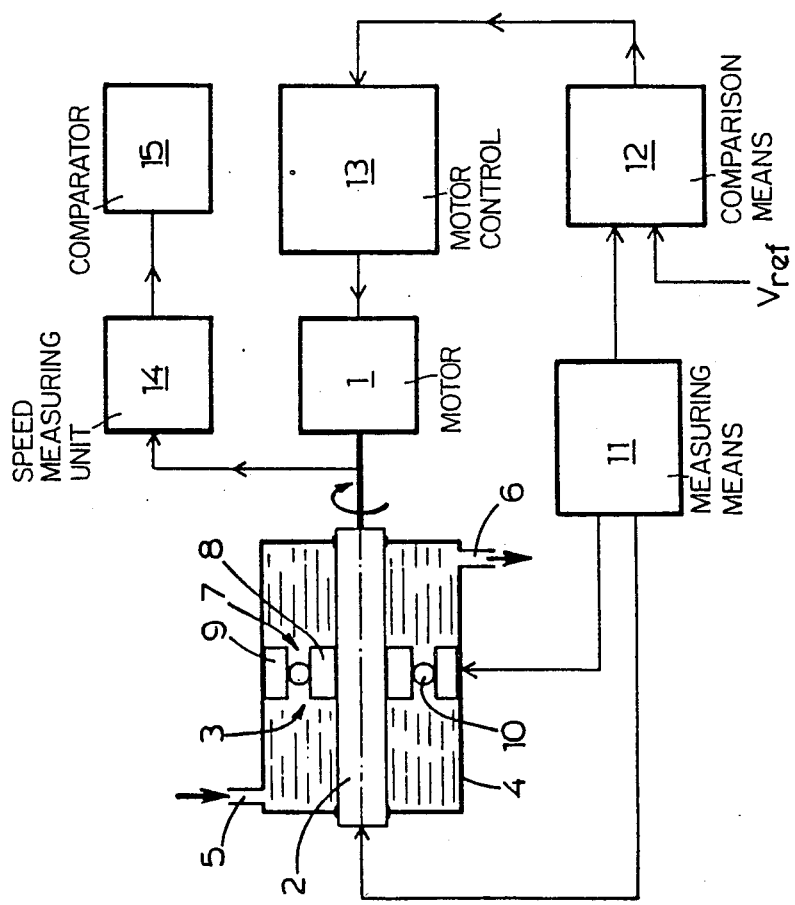

DEVICE FOR MEASURING THE EFFECTIVE VISCOSITY OF A LUBRICANT

BACKGROUND OF THE INVENTION

The invention relates to a device for measuring the effective viscosity of a lubricant, provided with a motor, a sensor capable of being driven by the motor, to which sensor the lubricant to be measured can be supplied, and a measuring element measuring a motor parameter the value of which corresponds to the viscosity of the lubricant.

In a known device of this kind, the sensor consists of a cylindrical rotor capable of being driven by the motor and suspended in a vessel containing the lubricant to be measured. Between the rotor and the inside wall of the vessel, there is a comparatively large clearance. The viscosity is determined by measuring the power that must be supplied to the motor to obtain a given motor speed. With this known device, only an average viscosity of the lubricant can be measured, which is inadequate for the purpose of determining the quality of the lubricant for bearing applications, since in bearings a lubricant is generally present only in a thickness of less than one micron. Particles present in the lubricant, ranging in size from greater than 0 to 30-50 microns, and gases, will vary greatly influence the viscosity of the lubricant in such a lubricant film, while hardly at all affecting the average viscosity measured with the known device.

The object of the invention is to provide a device in which the difficulties mentioned are avoided by simple yet effective means.

For this purpose, the device according to the invention is characterized in that the sensor consists of a bearing having two parts movable relative to each other, one of which parts is capable of being driven by the motor, and in that a control means is arranged to control the motor speed in such a way that at the time of being driven by the motor, no roughness contacts occur between the parts of the bearing, while the measuring element determines the motor speed and indicates that speed as a viscosity observation.

In this way, a device is achieved whereby the viscosity of the lubricant can be measured under conditions prevailing in the bearing, so that a timely signal is obtained whenever the viscosity of the lubricant reaches an unacceptable level.

The operation of the device according to the invention is based on the realization that in the absence of roughness contacts between the parts of the bearing, the so-called film parameter λ has a constant value (3), so that given the bearing constant C, which is a function of the viscosity and also depends on λ, by varying the motor speed so that no roughness contacts occur, the viscosity can be derived from said motor speed.

According to a simple embodiment of the invention, the control means is provided with a measuring means to measure the percentage contact time of the bearing, a comparison means comparing the percentage contact time with a predetermined reference value, and a motor control means that regulates the motor speed according to the output signal of the comparison means in such a way that the percentage contact time remains equal to the predetermined reference value.

BRIEF DESCRIPTION OF THE DRAWINGS

The invention will now be illustrated in more detail with reference to the drawing, which shows a block diagram of an embodiment of the device according to the invention.

DETAILED DESCRIPTION OF THE DRAWINGS

The device for measuring the viscosity of a lubricant is provided with a motor 1 coupled to a shaft 2. A sensor 3 is mounted in a housing 4 having an inlet 5 and an outlet 6 for the lubricant to be measured, which in this case consists of oil. The sensor 3 takes the form of a rotary bearing 7 whose inner race 8 supports the shaft 2 while the outer race 9 is connected to the housing 4; alternatively, of course, the shaft 2 may be mounted on two or more bearings. The bearing 7 further comprises conventional balls 10.

By passing the oil whose effective viscosity is to be measured in order to monitor its quality through the housing 4 by way of the inlet 5 and the outlet 6, the oil is made to lubricate the bearing 7, and its viscosity can be determined under the conditions prevailing in a bearing, much as they would prevail in the machine, or the like, whence the oil derives.

The measurement of the viscosity of the oil is based on the following.

It is known that for rolling contact in a bearing, the film parameter λ is given by $$\lambda = h_0/\sigma \quad (1)$$

where $h_0$=central oil film thickness;
$\sigma = \sqrt{r_1^2 + r_2^2}$, that is, the RMS value of the aggregate surface roughness of the opposed surfaces wherein $r_1$ and $r_2$ are the roughnesses of the two encountering bodies, i.e. the ball and its race ring.

It is known further that $h_o$ is given by $$h_o = C \times n^{0.7} \quad (2)$$

where
C=a value, constant at constant viscosity, depending on the bearing;
n=rotational speed in revolutions per minute.

It is known further that in the absence of roughness contact between the opposed lubricated surfaces, λ=3, so that it follows from equation (1) that:

$$h_o/\sigma = 3 \quad (3)$$

The absence of roughness contacts can be ascertained with a measuring 11 for measuring the percentage contact time of the bearing 7, which measuring means is known per se (see for example U.S. Pat. No. 4,471,295). From experiments, it has been found that λ is approximately 3 for a percentage contact time equal to 10%, which percentage contact time is well defined on the contact time/rotational speed diagram.

As has already been stated above, the bearing constant C is a function of the viscosity, so that we have $$C = K.f(v) \quad (4)$$

where $v$=viscosity.

If moreover it is ensured that λ=3, it follows from equations (1), (2) and (4) that $$3\sigma = K.f(v).n^{0.7} \quad (5)$$

so that n is given by $$n = [3\sigma/(K.f(\nu))]^{1/0.7} \quad (6)$$

Formula (6) shows that provided the percentage contact time is kept constant, the rotational speed is a measure of the viscosity of the oil. By also measuring the speed of the bearing, or of the motor, in the absence of roughness contacts, the viscosity $\nu$ is obtained by simple means. In the device described, this is accomplished as follows.

The output of the measuring means 11 for measuring the percentage contact, is connected to a comparison means 12, which compares the percentage contct time with a predetermined reference value $V_{ref}$ equivalent to 10% contact time. The output signal of the comparison means 12 is supplied to a motor control means 13 the output signal of which regulates the motor speed so that the percentage contact time measured by the measuring means 11 always remains equal to the predetermined reference value.

A measuring unit 14 is connected to the motor 1, determining the speed of the motor 1 and computing the viscosity from the speed by means of the formula (6). The output signal of the measuring unit 14 can be supplied to a comparator 15, which triggers an alarm signal when a predetermined threshold value is exceeded.

From the foregoing, it will be apparent that the invention provides a device of especially simple construction, by means of which the effective viscosity of lubricants can be measured under conditions such as prevail in a bearing.

The invention is not limited to the embodiment hereinbefore described by way of example, which may be modified in various ways within the scope of the invention.

We claim:

1. In a device for measuring the effective viscosity of a lubricant, comprising a motor, a sensor capable of beinbg driven by the motor, the sensor comprising means for supplying lubricant to be measured thereto, and a first measuring means for measuring a motor parameter that has a value corresponding to the viscosity of the lubricant, the improvement wherein the sensor is comprised of a bearing having two parts movable relative to one another, one of said parts being arranged to be driven by the motor, and further comprising regulating means for regulating the speed of said motor to maintain a condition in the bearing of no substantial roughness contacts between the parts of the bearing and wherein the regulating means comprises a second measuring means for measuring the percentage of contact time of the parts of the bearing with one another, a comparison means for comparing the percentage contact time with a predetermined reference value and for producing an output responsive thereto, and a motor control means for regulating the motor speed as a function of the output signal of the comparison means to maintain the percentage contact time equal to the predetermined reference value and wherein said first measuring means determines the motor speed and said first measuring means include means for indicating the viscosity as a function of said motor speed.

2. The device according to claim 1, wherein the reference value ($V_{ref}$) is equivalent to 10% contact time.

3. The device according to claim 1 wherein the first measuring means is connected to provide an output which is a function of the viscosity to a comparator.

4. The device according to claim 1 wherein the bearing is comprised of a rotary bearing mounted in a housing having an inlet and an outlet for the lubricant to be measured, the inner race of the bearing supporting a shaft driven by the motor.

* * * * *